United States Patent
Isenstein et al.

(10) Patent No.: US 7,906,337 B2
(45) Date of Patent: Mar. 15, 2011

(54) METHOD OF GENERATING AND USING BIOLOGICAL QUALIFICATION SLIDES TO QUALIFY BIOLOGICAL SCREENING DEVICES

(75) Inventors: Louise Isenstein, Carlisle, MA (US); Peter Albany, Groton, MA (US); Kimberly Lindfield, N. Reading, MA (US); Daniel C. Lapen, Lancaster, MA (US); Noorul Rahman, Ashland, MA (US)

(73) Assignee: Cytyc Corporation, Marlborough, MA (US)

( * ) Notice: Subject to any disclaimer, the term of this patent is extended or adjusted under 35 U.S.C. 154(b) by 1676 days.

(21) Appl. No.: 10/866,428

(22) Filed: Jun. 10, 2004

(65) Prior Publication Data
US 2004/0253144 A1    Dec. 16, 2004

Related U.S. Application Data

(60) Provisional application No. 60/478,208, filed on Jun. 12, 2003.

(51) Int. Cl.
*G01N 21/00* (2006.01)
*G01N 33/48* (2006.01)
*C12Q 1/04* (2006.01)

(52) U.S. Cl. ............................. 436/63; 422/561; 435/34

(58) Field of Classification Search ............. 422/58, 422/561; 435/34; 436/63
See application file for complete search history.

(56) References Cited

U.S. PATENT DOCUMENTS

| 5,168,066 | A | * | 12/1992 | Zahniser et al. | 436/63 |
| 5,828,776 | A | * | 10/1998 | Lee et al. | 382/133 |
| 5,889,880 | A | * | 3/1999 | Doerrer et al. | 382/128 |
| 6,026,174 | A | * | 2/2000 | Palcic et al. | 382/133 |

FOREIGN PATENT DOCUMENTS
WO    WO 0131566    *  5/2001

OTHER PUBLICATIONS

PCT International Search Report for PCT/US2004/017577, Applicant Cytyc Corporation, Forms PCT/ISA/210 and 220, dated Mar. 31, 2005 (5 pages).
PCT Written Opinion of the International Search Authority for PCT/US2004/017577, Applicant: Cytyc Corporation, Form PCT/ISA/237, dated Mar. 31, 2005 (5 pages).
Denaro Thomas J. et al, "PAPNET testing system: Technical update" Acta Cytologica, vol. 41, No. 1, 1997, pp. 85-73, XP008043486, ISSN: 0001-5547 (9 pages).

* cited by examiner

*Primary Examiner* — Lore Jarrett
(74) *Attorney, Agent, or Firm* — Vista IP Law Group LLP

(57) ABSTRACT

Kits and methods for qualifying automated biological screening system. At least one biological specimen having a plurality of marked target zones (MTZs) exhibiting an attribute is provided. The biological specimen(s) is processed through the automated biological screening system to determine locations of biological objects suspected of exhibiting the attribute. The locations of the MTZs can be compared to the locations of the suspicious biological objects in order to determine a number of matches. The automated biological screening system can then be qualified based on the number of matches, and optionally based on statistical information related to the biological specimen. The statistical information can be acquired by processing the biological specimen through a qualified automated biological screening system over a number of runs.

21 Claims, 9 Drawing Sheets

METHOD OF GENERATING AND USING BIOLOGICAL QUALIFICATION SLIDES TO QUALIFY BIOLOGICAL SCREENING DEVICES

RELATED APPLICATIONS

This application claims priority from provisional U.S. Patent Application Ser. No. 60/478,208, filed Jun. 12, 2003.

FIELD OF THE INVENTION

The present invention generally relates to methods for qualifying biological screening devices, and more particularly to methods for qualifying automated or semi-automated devices that screen biological specimens to facilitate identification of abnormal cell material.

BACKGROUND OF THE INVENTION

In the medical industry, there is often a need for a laboratory technician, e.g., a cytotechnologist, to review a cytological specimen for the presence of specified cell types. For example, there is presently a need to review a cervico-vaginal Papanicolaou (Pap) smear slides for the presence of malignant or pre-malignant cells. Since its introduction over fifty years ago, Pap smears have been a powerful tool for detecting cancerous and precancerous cervical lesions. During that time, the Pap smear has been credited with reducing mortality from cervical cancer by as much as 70%. This once precipitous drop in the death rate has slowed however, and the mortality rate in the United States for this preventable disease has remained virtually constant, at about 5,000 per year since the mid-eighties. Therefore, about one-third of the 15,000 women diagnosed with cervical cancer annually still die, because the cancer was detected too late. A further cause for concern is National Cancer Institute data that shows an annual 3% increase in the incidence of invasive cervical cancer in white women under 50 years of age since 1986.

A number of factors may be contributing to this current threshold, not the least of which is the fact that many women, particularly in high risk populations, are still not participating in routine cervical cancer screening. Another contributing factor that has received much attention is the limitation of the traditional Pap smear method itself.

The reliability and efficacy of a cervical screening method is measured by its ability to diagnose precancerous lesions (sensitivity) while at the same time avoiding false positive diagnosis (specificity). In turn, these criteria are dependent on the accuracy of the cytological interpretation. The conventional Pap smear has false negative rates ranging from 10-50%. This is due in large part to the vast number of cells and objects (typically as many as 100,000 to 200,000) that must be reviewed by a technician to determine the possible existence of a small number of malignant or pre-malignant cells. Thus, Pap smear tests, as well as other tests requiring detailed review of biological material, have suffered from a high false negative rate due to fatigue imposed on the technician.

To facilitate this review process, automated biological screening (ABS) systems have been developed to focus the cytotechnologist's attention on the most pertinent cells, with a potential to discard the remaining cells from further review. A typical ABS system includes an imager, processor and automated viewing microscope. The imager acquires a series of images of a specimen slide, each image depicting a different portion of the slide. The processor then processes these images to identify the most pertinent biological objects for subsequent viewing by a technician, and their locations (x-y coordinates) on the slide. This information is then passed onto the microscope, which automatically proceeds to the x-y coordinates and centers on the biological objects for review by the technician. Alternatively, images of suspicious biological objects may be presented for viewing on a monitor.

Oftentimes, a particular ABS system must be qualified, (e.g., during the manufacturing processes and when repairing the systems in the field) to ensure that it consistently provides accurate results. Typically, an ABS system is qualified by processing a large number of abnormal biological specimens with the system, and then performing a two-armed test. That is, the results generated by the system are compared to results achieved from performing a thorough manual review of the specimen by a cytologist. For example, the locations of the suspicious biological objects found by the system will be compared to the locations of the actual abnormal biological objects obtained from manual review. If a certain number of matches is achieved, the system is qualified.

Although the two-armed test has, in general, been a successful tool for qualifying ABS systems, it requires a slow and tedious process due to the large amount of data that must be manually processed. In essence, the work and time required to qualify a single ABS system amounts to a "mini clinical trial." In addition, cytologists, who are not readily available to organizations where these tests are often performed, must be involved in the two-arm test. As such, the performance of these two-arm tests are often administratively difficult.

There thus remains a need to provide a quicker and more efficient process for qualifying ABS systems.

SUMMARY OF THE INVENTION

In accordance with a first aspect of the invention, a kit for qualifying an automated biological screening (ABS) system is provided. The ABS system can be any automated screening system (including semi-automated screening systems) that screens biological specimens for specific attributes. For example, the ABS system can be a screening system that screens vaginal-cervico specimens for any abnormal cells, e.g., those classified in one of the major categories defined by The Bethesda System for Reporting Cervical/Vaginal Cytologic Diagnosis.

In a preferred embodiment, the kit comprises at least one slide carrying a biological specimen with a plurality of marked target zones (MTZs) exhibiting an attribute. The slide (s) are evaluated by the automated biological screening system to determine locations of biological objects suspected of exhibiting the attribute. The attribute can be any characteristic of interest, for example, a cell abnormality, such as those classified by The Bethesda System for Reporting Cervical/Vaginal Cytologic Diagnosis.

The kit further comprises a medium that stores known locations of the MTZs. The medium can take the form of any structure that can store data, including a piece of paper, but in a preferred embodiment is a computer medium. The medium can optionally store statistical information relating to the MTZs, e.g., a number of match counts between the known locations of the MTZs and the locations of suspected biological objects obtained from at least one other automated biological screening system. The statistical data can take the form of a means and/or tolerance intervals. For example, a tolerance interval can be defined, such that 95% of the population is included within the tolerance interval at at least a 99 percent confidence level.

The kit further comprises computer software containing instructions, which when executed, compare the known locations of the MTZs to the locations of the suspicious biological objects in order to determine a number of matches. In one embodiment, when executed, the instructions further indicate that the ABS system is qualified based on the number of matches. Optionally, the instructions, when executed, indicate that the ABS system is qualified based further on statistical information.

In accordance with another aspect of the invention, a method of qualifying an ABS system is provided. The method comprises providing at least one biological specimen having a plurality of MTZs exhibiting an attribute, and processing the biological specimen(s) through the ABS system to determine locations of biological objects suspected of exhibiting the attribute. The attribute can be any characteristic of interest, such as a cell abnormality, as previously discussed. The biological specimen(s) can be presented to the ABS system on a microscope slide or any other device that is compatible with the ABS system. The method further comprises comparing the locations of the MTZs to the locations of the suspicious biological objects in order to determine a number of matches. In one embodiment, the ABS system is qualified based on the number of matches, and optionally statistical information, such as the type previously described.

In accordance with still another aspect of the invention, a method of generating statistical information for a biological specimen is provided. The method comprises providing at least one biological specimen having a plurality of marked target zones (MTZs) exhibiting an attribute. The method further comprises processing the biological specimen(s) through at least one automated biological screening system over a number of runs, wherein locations of biological objects suspected of exhibiting the attribute are determined for each processing run. The attribute can be any characteristic of interest., such as a cell abnormality or a physical characteristic indicative of a likelihood of such abnormality. The biological specimen(s) can be presented to the ABS system(s) on a slide or any other device that is compatible with the ABS system(s). The method further comprises comparing the locations of the MTZs to the locations of the suspicious biological objects in order to determine a number of matches for each run, and generating statistical information based on the number of matches for each run.

BRIEF DESCRIPTION OF THE DRAWINGS

The drawings illustrate the design and utility of a preferred embodiment of the present invention, in which similar elements are referred to by common reference numerals and in which.

DETAILED DESCRIPTION OF PREFERRED EMBODIMENTS

Figure 1:
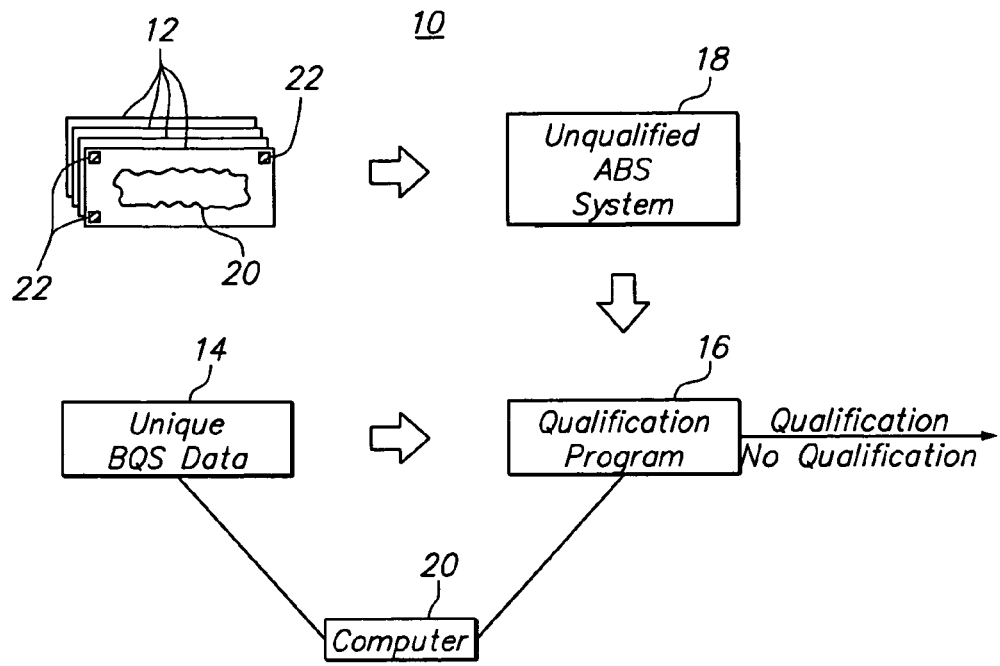
FIG. 1 is a block diagram of a qualification kit constructed in accordance with one preferred embodiment of the present invention.

With reference to FIG. 1, a qualification kit 10 assembled in accordance with one embodiment of the invention, will now be described. The kit 10 generally comprises (1) a set of specially prepared and selected biological qualification slides (BQSs) 12 (in this case, four) that carry known abnormal cells; (2) associated BQS data 14 comprising unique abnormal cell location and statistical information for each BQS 12; and (3) a qualification program 16 for qualifying the automated biological screening (ABS) system 18 based on a comparison between data resulting from processing the BQSs 12 through the ABS system 18 and the unique BQS data 16.

Each of the BQSs 12 carries a biological specimen 20 containing abnormal cells, e.g., those classified in one of the major categories defined by The Bethesda System for Reporting Cervical/Vaginal Cytologic Diagnosis, including Low Grade Squamous Intraepithelial Lesions (LGSIL), High Grade Squamous Intraepithelial Lesions (HGSIL), Squamous Cell Carcinoma, Adenocarcinoma, and Adenocarcinoma in situ (AIS). The locations of these abnormal cells have been marked by trained personnel, such as cytotechnologists and/or pathologists. These locations, referred to as marked target zones (MTZs), are used to generate the unique BQS data 14. Each BQS 12 comprises fiducial marks 22, which will be used to correlate the different coordinate systems used during the performance of various functions on the BQS 12, as will be described in further detail below.

Preferably, the qualification program 16 is stored on a computer disk with read only memory (CD-ROM) and is designed to run on an ordinary off-the-shelf laptop or desktop personal computer (PC) 20 with a Windows® operating system. The qualification program 16, however, can be stored on any medium and be designed to run on any suitable platform.

As will be described in further detail below, an ABS system identical to the ABS system 18, with the exception that it has already been qualified, will be used to provide the statistical information that will be subsequently used to generate the unique BQS data 14. The unique BQS data 14 will eventually be loaded into the same computer in which the qualification program 16 will be installed, i.e., the computer 20. The unique BQS data 14 can be stored on any suitable medium. For example, the medium can be simply a piece of paper on which the unique BQS data 14 is recorded and then subsequently manually entered into the computer 20 when prompted by the qualification program 16. Preferably though, the medium on which the unique BQS data 14 is stored is a computer medium, e.g., a CD-ROM, in which case, the unique BQS data 14 can be automatically loaded into the computer 20 after receiving a prompt from the qualification program 16. Even more alternatively, the medium on which the BQS data 14 is stored can be remotely located, in which case, the unique BQS data 14 can be downloaded from a remote source, such as, the manufacturer of the ABS system 18. If practical, the medium on which the unique BQS data 14 is stored can be the same medium on which the qualification program 16 is stored, in which case, the unique BQS data 14 will be loaded on the computer 20 with the qualification program 16 is installed.

I. Automated Biological Screening System

Before discussing processes used to generate BQSs 12 and the associated unique BQS data 14 and subsequently qualify the ABS system 18, it will be helpful to describe a preferred embodiment of the ABS system 18.

Figure 3:
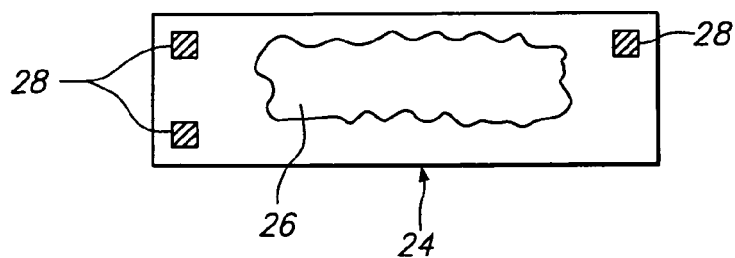
FIG. 3 is standard microscope slide carrying a biological specimen.
Figure 2:
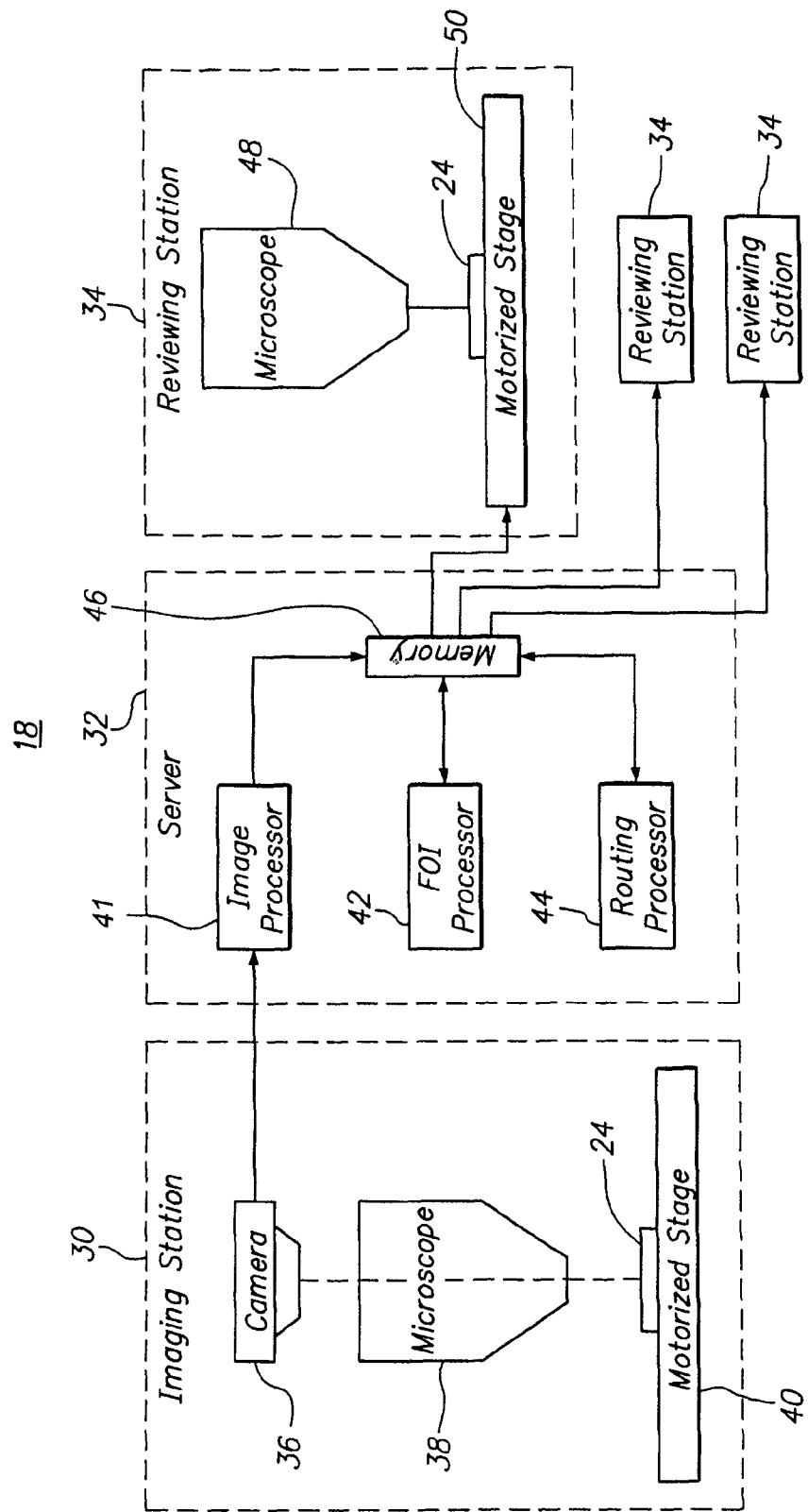
FIG. 2 is a block diagram of one automated biological screening (ABS) system that can be qualified using the qualification kit of FIG. 1.
Figure 4:
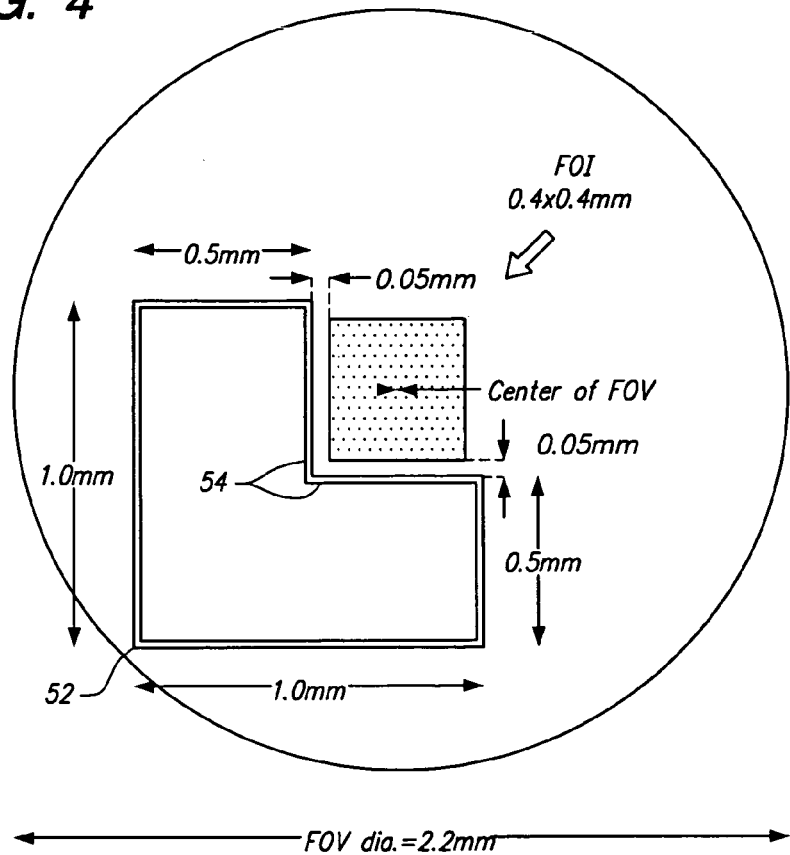
FIG. 4 is a view of a field of interest and marker indicator as shown through a field of view of a microscope used in the system of FIG. 2.

Referring to FIG. 2, the ABS system 18 is configured for presenting a biological specimen 26 located on a microscope slide 24 (best shown in FIG. 3) to a technician, such as a cytotechnologist, who can then review objects of interest (OOIs) located within the biological specimen. The OOIs are arranged in a number of fields of interest (FOIs) (one of which is illustrated in FIG. 4) that cover portions of the slide 24, so that the cytotechnologist's attention can be subsequently focused on OOIs within the FOIs, rather than slide regions that are not pertinent. The slide 24 comprises fiducial marks 28, which will be used to ensure that the x-y coordinates of the slide 14 during the review process can be correlated to the x-y coordinates of the slide 14 obtained during the imaging process.

Although the system 18 can be used to present any biological specimen (or even a non-biological specimen, such as a computer chip) that requires further review, the system 18 lends itself particularly well to the presentation of cytological cervical or vaginal material, such as that typically found on a Pap smear slide. In this case, the OOIs take the form of individual cells and cell clusters that are either suspected to have an abnormal condition; such as malignancy or pre-malignancy (e.g., LGSIL, HGSIL, Squamous Cell Carcinoma, Adenocarcinoma, and AIS), or otherwise have attributes indicating the relative highest risk of such abnormal condition within the specimen. The biological specimen 26 will typically be placed on the slide 24 as a thin cytological layer. Preferably, a cover slip (not shown) is adhered to the specimen 26, thereby fixing the specimen 26 in position on the slide 24. The specimen 26 may be stained with any suitable stain, such as a Papanicolaou stain.

The system 18 generally comprises (1) an imaging station 30 for acquiring images of the biological specimen on the slide 24, and generating electronic image data from the images; (2) a server 32 for filtering and/or processing the electronic image data to identify OOIs and for assigning one or more of the OOIs to each of a plurality of FOIs; and (3) a plurality of reviewing stations 34 (3 shown), each of which provides a field of view (FOV) (illustrated in FIG. 4) that is scanned relative to each FOI in order to present the OOIs to the cytotechnologist. The system 18 may also comprise a user interface (not shown), including a monitor, keyboard, and mouse (all not shown), so that the cytotechnologist can interact with the system 18.

The imaging station 30 is configured to image the slide 24, which is typically contained within a cassette (not shown) along with other slides. During the imaging process, the slides 24 are removed from the respective cassettes, imaged, and then returned to the cassettes in a serial fashion. In the illustrated embodiment, the imaging station 30 is capable of processing up to 10 cassettes, each holding up to 25 slides, in about 16 hours.

The imaging station 30 comprises a camera 36, a microscope 38, and a motorized stage 40. The camera 36 captures magnified images of the slide 24 through the microscope 38. The camera 36 may be any one of a variety of conventional cameras, such as a charge coupled device (CCD) camera, which alone or in conjunction with other components, such as an analog-to-digital (A/D) converter, can produce a digital output of sufficient resolution to allow processing of the captured images, for example a digital image having a resolution of 640×480 pixels. Preferably, each pixel is converted into an eight-bit value (0 to 255) depending on its optical transmittance, with "00000000" being the assigned value for least amount of light passing through the pixel, and "11111111" being the assigned value for a greatest amount of light passing through the pixel.

The slide 24 is mounted on the motorized stage 40, which scans the slide 24 relative to the viewing region of the microscope 38, while the camera 36 captures images over various regions of the biological specimen 26. The shutter speed of the camera 36 is preferably relatively high, so that the scanning speed and/or number of images taken can be maximized. The motorized stage 40 keeps track of the $x$-$y$ coordinates of the slide 24, and thus the images as they are captured by the camera 36. For example, encoders (not shown) can be coupled to the respective motors of the motorized stage 40 in order to track the net distance traveled in the x- and y-directions during imaging. These coordinates are measured relative to the fiducial marks 28 affixed to the slide 24 (shown in FIG. 3). As will be described in further detail below, these fiducial marks 28 will also be used by the reviewing station 34 to ensure that the x-y coordinates of the slide 24 during the review process can be correlated to the x-y coordinates of the slide 24 obtained during the imaging process.

The server 32 comprises (1) an image processor 41 that is configured to obtain the OOIs from the image data acquired from the camera 36; (2) a FOI processor 42, which is configured to assign OOIs to each FOI; (3) a routing processor 44, which is configured to map routing path that the reviewing station 34 will use to scan from one FOI to the next; and (4) a memory 46 configured for storing the OOIs and FOIs, the ranking and x-y coordinates of the OOIs, and the routing path for the FOIs. It should be appreciated that the functions performed by the respective processors 41, 42, and 44 can be performed by a single processor, or alternatively, performed by more than one processor. Likewise, it can be appreciated that the memory 46 can be divided into several memories.

The image processor 41 identifies and determines the locations of OOIs within the biological specimen 26 by manipulating digital images received from the camera 36 in a suitable manner. In one embodiment, the image processor 41 accomplishes this by using various segmentation and classification operations, the details of which are described in copending Provisional Application Ser. No. 60/478,431, entitled "Method and System for Organizing Multiple Objects of Interest in Field of Interest," which is expressly incorporated herein by reference in its entirety.

For each digital image, the image processor 41 than stores the OOIs, along with their ranking and coordinates, within the memory 46 as a frame data record (FDR). In the illustrated embodiment, approximately 2000 digital images are obtained for each slide 24,and thus approximately 2000 FDRs may be stored in memory 46 for each slide 24. In the illustrated embodiment, the image processor 40 limits the number of OOIs contained in each FDR to 10 for individual OOIs and 3 for clustered OOIs.

The FOI processor 42 defines FOIs based on the x-y coordinates of the OOIs. In the illustrated embodiment, twenty-two FOIs are defined, twenty of which are reserved for individual OOIs, and two of which are reserved for clustered OOIs. In one embodiment twenty FOIs are centered over 20 highest ranked individual OOIs, and the remaining two FOIs are centered over the 2 highest ranked clustered OOIs. Alternatively, the FOIs are defined in a manner that avoids inclusion of OOIs in a FOI that are already included within another FOI. In this manner, the OOIs can be grouped within the FOIs in a coordinated manner, so that the number of OOIs that are included within FOIs can be maximized. Alternatively, if the number of FOIs is not fixed, the number of FOIs required to include all of the OOIs can be minimized. Further details on this alternative method of defining FOIs is described in above-incorporated provisional application Ser. No. 60/478,431.

After the FOIs have been generated, the FOI processor 42 stores the x-y coordinates of all of the FOIs in memory 46 for later use by the routing processor 44. Specifically, the routing processor 44 maps the x-y coordinates of the FOIs using a suitable routing algorithm, such as a modified "traveling salesman" algorithm, which determines the most efficient viewing route for presenting the FOIs in the reviewing station 34. The routing processor 44 then stores the x-y coordinates of the FOIs, along with the routing plan, in memory 46 for subsequent access by the reviewing station 34.

A total of three reviewing stations 34 are shown coupled to the server 32, so that up to three cytotechnologists have simultaneous access to the pertinent information stored in the server 32. Notably, the system 18 can typically process the slides 24 much quicker than a cytotechnologist can review them. Even if the specimen processing speed of the system 10 is slower than the specimen review speed of a cytotechnologist, the system 18 can generally be operated 24 hours a day, whereas the typical cytotechnologist will only work 8 hours a day. Thus, the bottleneck in the screening process occurs at the human level, i.e., the detailed review of the biological material contained on the slides 24. Thus, it can be appreciated that the use of multiple reviewing stations 34 alleviates this bottleneck, thereby providing for a much more efficient process.

Before discussing the details of the reviewing stations 34, reference is made to FIG. 4, which illustrates an exemplary FOV that each reviewing station 34 centers over a FOI. In the illustrated embodiment, the FOV has a diameter of 2.2 mm, and the FOI is defined by a 0.4 mm×0.4 mm square circumscribed by the FOV. In the actual embodiment, the borders of the FOI are imaginary and cannot be seen, so that the cytotechnologist's view of any OOIs is not obstructed. In order to more quickly direct the cytotechnologist's attention to the FOI and to provide a reference that generally indicates the exact region bound by the imaginary borders of the FOI, an L-shaped mark indicator 52 is provided. The mark indicator 52 captures the FOI (i.e., an open square portion 54 of the mark indicator 52 borders the left and bottom sides of the FOI). A 0.05 mm margin is provided between the mark indicator 52 borders and the imaginary borders of the FOI, so that the portions of OOIs extending outside of the left and bottom borders of the FOI (resulting from an OOI that is included within the FOI, but centered near the left or bottom border of the FOI) will not be obstructed by the mark indicator 52. The mark indicator 52 also serves to provide a means for the cytotechnologist to electronically mark the FOI (e.g., by pushing a button that electronically colors the mark indicator 52) as requiring further review by a pathologist (e.g., if an OOI has malignant or pre-malignant attributes).

Referring back to FIG. 2, each reviewing station 34 comprises a microscope 48 and a motorized stage 50. The slide 24 (after image processing) is mounted on the motorized stage 50, which moves the slide 24 relative to the viewing region of the microscope 48 based on the routing plan and x-y coordinates of the FOIs obtained from memory 46. Specifically, these x-y coordinates, which were acquired relative to the x-y coordinate system of the imaging station 118, will be transformed into the x-y coordinate system of the reviewing station 34 using the fiducial marks 28 affixed to the slide 24 (shown in FIG. 3). Thus, it is ensured that the x-y coordinates of the slide 24 during the reviewing process are correlated to the x-y coordinates of the slide 24 during the imaging process. The motorized stage 50 will then move in accordance with the transformed x-y coordinates of the FOIs, as dictated by the routing plan. In the illustrated embodiment, to advance from one FOI to another, the cytotechnologist presses an activation switch (not shown). In this sense, the reviewing station 34 is semi-automatic. Alternatively, the FOIs are automatically advanced from one to the next. In this case, the motorized stage 50 may optionally pause for a predetermined amount of time for each FOI. In this sense, the reviewing station 34 is fully automatic.

As the selected FOIs are presented in the FOV of the microscope 48, the cytotechnologist reviews the FOIs and makes decisions about the level of cell abnormality, if any. The cytotechnologist will then electronically mark any FOIs that are suspect. The cytotechnologist can preferably return to a previously viewed FOI, and manually move to (and view) locations on the slide not encompassed by FOIs. Following review of the slide 24, if any of the FOIs have been marked by the cytotechnologist, the reviewing station 34 automatically scans the entire biological specimen 26, so that 100% viewing coverage is ensured. The cytotechnologist is able to pause the autoscan and to move the stage 50 in order to reposition and access locations on the slide 24, as desired.

II. Procedure for Generating Biological Qualification Slides

Figure 5:
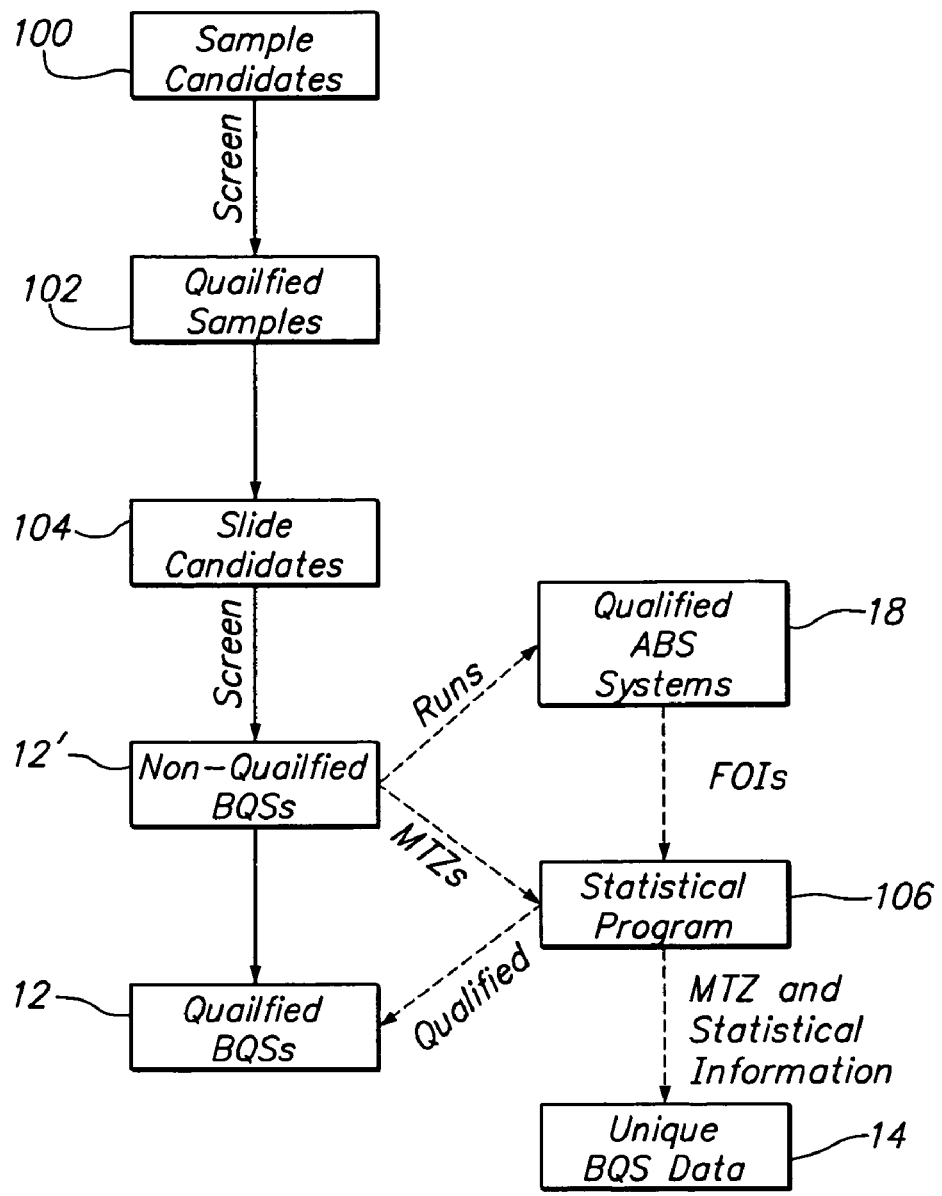
FIG. 5 is a generalized flow diagram illustrating a process used to generate biological qualification slides (BQSs) and unique BQS data illustrated in the qualification kit of FIG. 1.

With reference to FIG. 5, a preferred generalized process for generating BQSs 12 will now be described. First, sample candidates 100 will be prepared and screened, resulting in samples 102 from which the BQSs will be eventually generated. Next, slide candidates 104 will be generated from the samples 102 and prescreened, resulting in non-qualified BQSs 12' with MTZs. Next, the non-qualified BQSs 12' are processed through one or more qualified ABS systems 18' over a number of runs, resulting in sets of FOIs, each one corresponding to a different run. A statistical program 106 then generates statistical information for each non-qualified BQS 12' based on matches between each set of FOIs and the MTZs located on the non-qualified BQS 12'. The statistical program 106 analyzes the statistical information for a set of non-qualified BQSs 12', resulting in a set of qualified BQSs 12 and the associated unique BQS data 14, which contains the MTZ location information and statistical information for each of the qualified BQSs 12 in the set.

With reference to FIGS. 6-10, a preferred method of generating BQSs 12 will be described. In this example, the BQSs 12 will be generated for ABS systems 18 that screen cervical-vaginal specimens, such as Pap smears, for malignant and pre-malignant conditions.

A. Generation of Samples

Prior to the actual generation of BQSs 12, the samples from which the BQSs 12 will be generated and preferably screened to ensure that each sample contains a certain percentage range of abnormal cells, which in a cervical-vaginal specimen, can be referred to as ASCUS+ cells (i.e., Atypical Squamous Cell of Undetermined Significance or higher risk, including LGSIL, HGSIL, Squamous Cell Carcionoma, Atypical Glandular cells of Undetermined Significance (AGUS), AIS, and Adenocarcinoma. Too low or too high of an ASCUS+ cell percentage will result in an abnormal statistical distribution, as will be described in a different section below. For purposes of brevity and clarity, the following sample screening process is described in the context of a single sample candidate. It should be appreciated, however, that a typical process will result in multiple sample candidates that can either be generated serially or in parallel.

Figure 6:
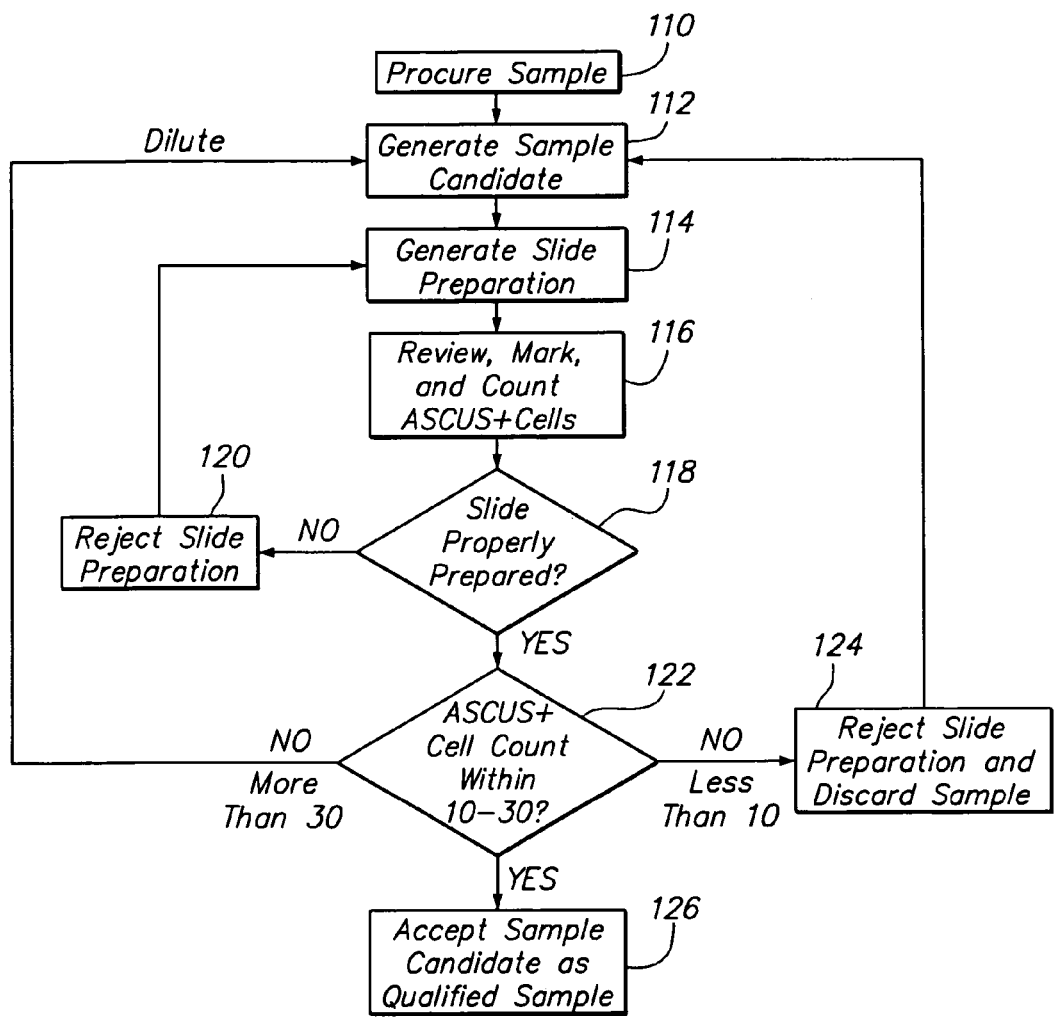
FIG. 6 is a flow diagram illustrating a process used to generate a sample from which the BQSs will eventually be generated.

Referring now to FIG. 6, the sample pre-screening process is initiated by procuring various gynecological samples (e.g., from material discarded from hospitals and clinical laboratories) and/or malignant cell cultures (action block 110). Next, a sample candidate is prepared from any of the gynecological samples and/or malignant cell cultures (action block 112). For example, an individual gynecological sample candidate should have a diagnosis of LGSIL+, i.e., LGSIL or higher risk (HSIL, Squamous Cell Carcionoma, AGUS, AIS, and Adenocarcinoma). A mixed sample candidate may consist of LGSIL+ samples, or malignant cell culture or LGSIL+ samples diluted with gynecological samples that are negative for intraepithelial lesion or malignancy in order to provide the necessary concentration of abnormal cells. The resulting sample candidate will be contained in a labeled vial.

From the sample candidate, a slide preparation is made using a standard procedure, e.g., using a qualified gynecological TransCyt® filter and qualified ThinPrep® 2000 or ThinPrep® 3000 processor, which can be obtained from Cytyc Corporation, located in Boxborough, Mass. (action block 114). The slide preparation is then stained with a qualified stain, e.g., one or more of the ThinPrep® staining solutions obtained from Cytyc Corporation.

Next, the slide preparation is manually reviewed on a microscope, preferably by at least two cytotechnologists, in order to mark and count the locations of abnormal cells (action block 116), which in a preferred method, are ASCUS+ cells. The cytotechnologists can conveniently utilize the reviewing station of a qualified ABS system 18'. In this case, the reviewing station will be operated in the manual mode when reviewing the slide preparation.

Next, it is determined whether the slide preparation has been properly prepared (decision block 118). For example, a slide preparation that has not been diagnosed by the cytotechnologists with LSIL+, has scant cellularity, contains predominantly red or white blood cells, or contains extensive mucus or cytolysis, will be considered to be not usable for the qualification process. If it is determined that the slide preparation is not usable for the qualification process, the slide preparation is rejected (action block 120), and the process returns to action block 114, where another slide preparation is generated from the sample candidate.

If it is determined that the slide preparation has been properly prepared, the ASCUS+ cell count will be compared to a predetermined range, which in the illustrated embodiment, is a range between 10 and 30 ASCUS+ cells (decision block 122). In this manner, it can be determined whether the sample candidate from which the corresponding slide preparation was prepared, has a sufficient percentage of ASCUS+ cells.

Figure 7:
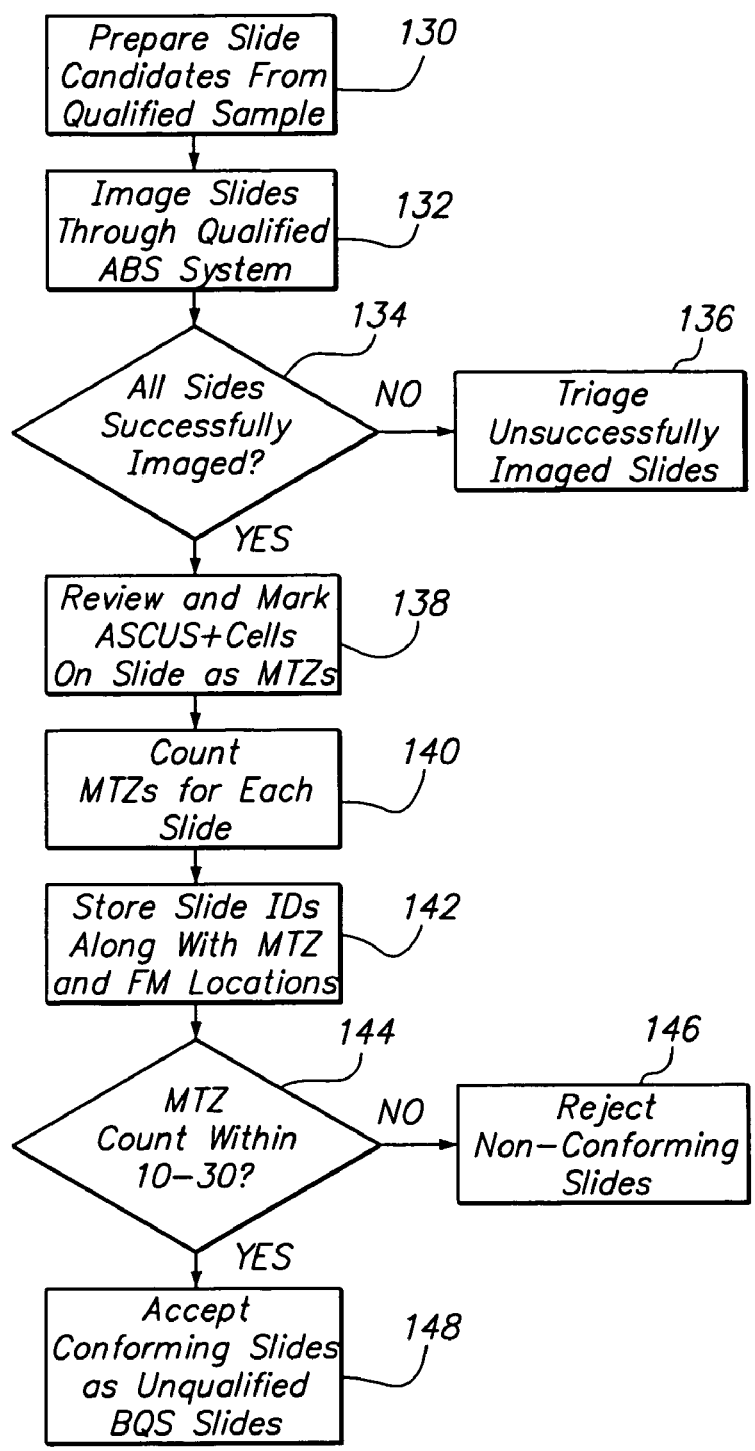
FIG. 7 is a flow diagram illustrating a process used to generate non-qualified BQSs that may be subsequently qualified.

If a slide preparation has less than 10 ASCUS+ cell locations, the corresponding sample candidate will be rejected, and the corresponding sample candidate will be discarded (action block 124). The process will then return to action block 112, where another sample candidate is prepared. If a slide preparation has more than 30 ASCUS+ cell locations, the process will return to action block 112, where the corresponding sample candidate can be further diluted to reduce the ASCUS+ cell percentage. If a slide preparation has between 10 and 30 ASCUS+ cells, the sample candidate is accepted as a sample (action block 126), and is then used to generate non-qualified BQSs 12', as shown in FIG. 7.

B. Generation of Non-Qualified BQSs

Once a sample has been identified, multiple non-qualified BQSs can be generated from the sample. Referring now to FIG. 7, a multitude of slide candidates are prepared from the sample (action block 130), preferably in the same manner as the sample preparation in action block 114 of FIG. 6. As will be described in further detail below, the slide candidates that pass a predetermined set of criteria will subsequently become BQSs 12.

The slide candidates are then imaged by a qualified ABS system 18', which generates FOIs and routing paths for each slide candidate (action block 132). If any slide candidate has been imaged unsuccessfully (decision block 134), the rejected slide candidate will be triaged (action block 136). The details of this triaging process will be described in further detail below. If all slide candidates have been imaged successfully (decision block 134), a cytologist will review the slide candidates and electronically mark the locations of all cells and cell clusters that have a diagnosis of ASCUS+ (action block 138). Preferably, the cytologist will use the autoscan function of a qualified ABS system 18' when reviewing the slide candidates. The electronically marked locations will be considered MTZs (i.e., marked target zones). For each slide candidate, the cytologist then counts the number of MTZs (action block 140).

The slide candidate will then be assigned a slide identification (ID), and it, along with the locations of the MTZs downloaded from the qualified ABS system 18', will be stored in a computer archive file, preferably on a CD-ROM (action block 142). Notably, each side candidate has fiducial marks similar to the fiducial marks 28 disposed on the slide 24 of FIG. 3. The locations of these fiducial marks will also be stored in the computer archive file to ensure that the x-y coordinates of the MTZs on the slide candidate during this review process can be correlated to the x-y coordinates of the MTZs on the slide candidate (assuming that it is used as a BQS 12) during the review process performing during system qualification, as will be described in further detail below.

If the count for MTZs that have ASCUS+ cells is outside the range of 10 to 30 (decision block 144), the non-conforming slide candidates are discarded (action block 146). If the count for MTZs that have LSIL+ cells is within the range of 10 to 30 (decision block 148), the conforming slide candidates are accepted as non-qualified BQS slides (action block 148), which may eventually become qualified in the BQS generation process illustrated in FIG. 7.

Figure 8:
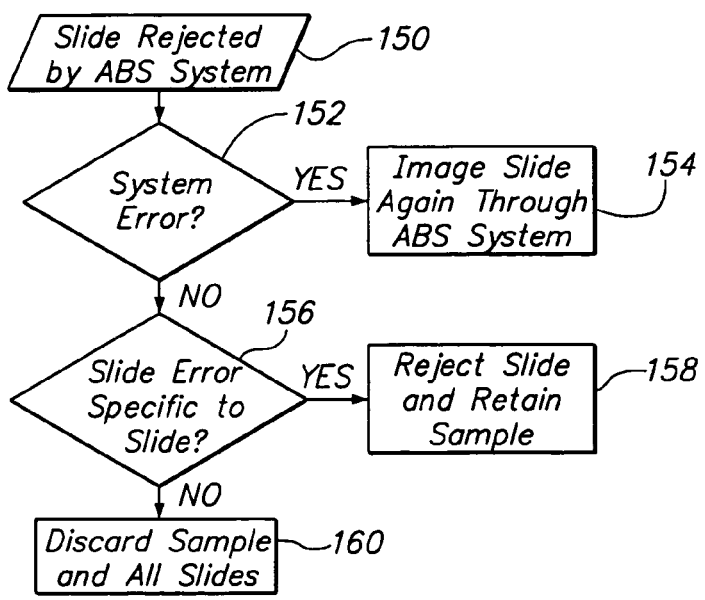
FIG. 8 is a flow diagram illustrating a process used to triage a rejected slide.

Referring to FIG. 8, an unsuccessfully imaged slide candidate will be triaged as follows. After the slide candidate has been rejected by the qualified ABS system 18' (status block 150), the cytologist determines if a system error caused the rejection (decision block 152). If so, the qualified ABS system 18' is repaired or adjusted as necessary, and slide candidate is imaged again (action block 154). If not, it is assumed that a slide error caused the rejection. In this case, the technician determines whether the slide error is specific to the slide (decision block 156). If so, the slide candidate is rejected, and the sample from which it was generated is retained (action block 158). If not, it is assumed that the error was caused by the sample, which is then discarded along with all slides generated from the sample (action block 160).

C. Generation of BQSs and Corresponding Unique BQS Data

Figure 9:
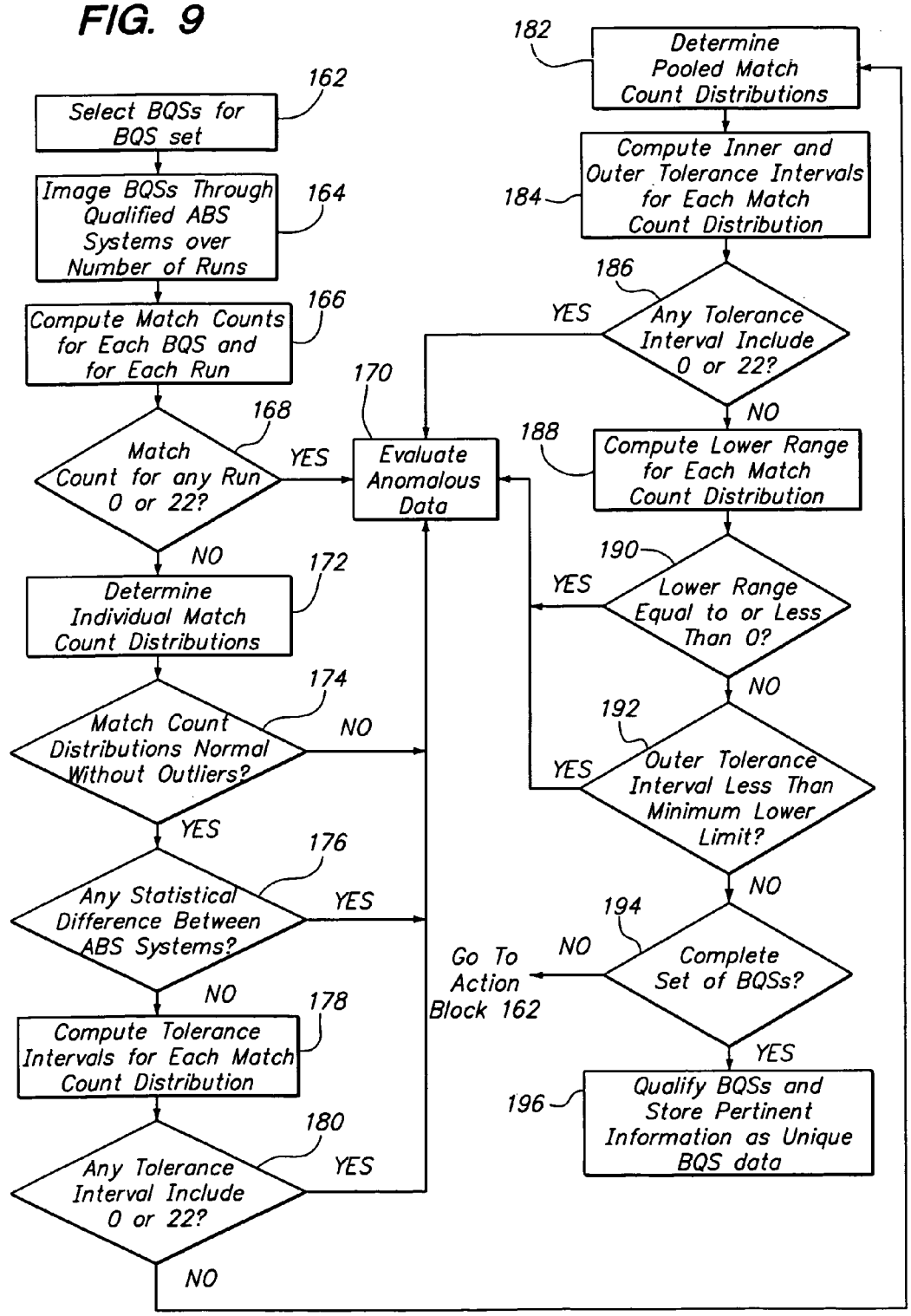
FIG. 9 is a flow diagram illustrating a process used to qualify the non-qualified BQS and generate corresponding unique BQS data.

Once the non-qualified BQS 12' have been generated they can be qualified based on statistical information generated from the non-qualified BQSs 12'. Referring now to FIG. 9, a set of the non-qualified BQSs 12' (in the illustrated embodiment, four) is initially selected (action block 162). Each non-qualified BQS 12' in the set is then imaged with at least one qualified ABS system 18' (three in a preferred method) over a number of runs (125 runs in a preferred method) (action block 164). Thus, there will be a total of 375 runs (assuming, three qualified ABS systems 18' are used) for each non-qualified BQS 12'. Each qualified ABS system 18' identifies OOIs on each non-qualified BQS 12' and subsequently generates FOIs to include the OOIs for each run.

For each run, the statistical program 106 calculates the number of MTZ matches to obtain a MTZ match count for each non-qualified BQS 12' (action block 166). Thus, there will be a total of 375 MTZ match counts (125 for each qualified ABS system 18') for each non-qualified BQS 12'. Specifically, the statistical program 106 compares the x-y coordinates of the MTZs (obtained from the archive file generated in the process flow of FIG. 7) to the x-y coordinates of the FOIs (downloaded from the qualified ABS systems 18') to determine if each FOI is adjacent to a MTZ.

Figure 11:
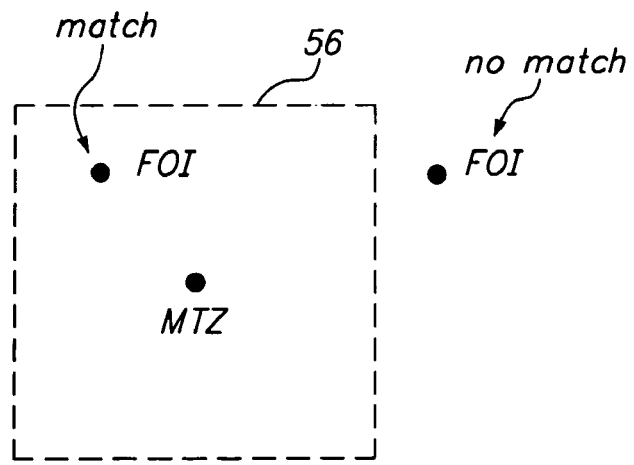
FIG. 11 is a plan view illustrating two fields of interests (FOIs), one location of which is deemed to match the location of the marked target zone (MTZ), and the other location of which is deemed not to match the location of the MTZ.

In a preferred method, a FOI is considered adjacent to a MTZ by centering an imaginary boundary box 56 (e.g., measuring 500 μm×500 μm) on the x-y coordinates of the MTZ, as illustrated in FIG. 11, and determining if the x-y coordinates of the FOI fall within the boundary box 56. If so, a MTZ match is identified, and if not, a MTZ is not identified. It should be noted that prior to this comparison, the coordinate system in which the x-y coordinates of the MTZs were acquired (MTZ coordinate system) must first be correlated to the coordinate system in which the x-y coordinates of the FOIs were generated (FOI coordinate system). The statistical program 106 accomplishes this by obtaining the coordinates of the fiducial marks from the archive file, and then using them to transform the x-y coordinates of the MTZs into the FOI coordinate system.

For each non-qualified BQS 12', the statistical program 106 next determines if the MTZ match count for any run is 0 or 22 (decision block 168). If so, the anomalous data will be evaluated (action block 170), the detailed steps of which will be described in further detail below with reference to FIG. 10. If not, the statistical program 106 collects the statistical MTZ match count data generated from each qualified ABS system 18' and for each non-qualified BQS 12', and determines the individual match count distributions (a total of 12) (action block 172). The statistical program 106 then determines if each individual match count distribution is normal and has a minimal amount of outliers (less than 1%) (decision block 174).

Specifically, the statistical program 106 generates the normal probability plot and the Pearson Product-Moment correlation of the normal probability plot for each corresponding individual match count distribution. If the correlation coefficient is greater than 0.9, then the individual match count distribution is approximately normal. The statistical program 106 computes the mean and the standard deviation for each individual match count distribution. The statistical program 106 then determines the number of outlier data points for each individual match count distribution. A data point is an outlier data point if it is greater than the mean ±3 standard deviations. If any of the individual match count distributions is not normal or contains 1% or more outlier data points, the anomalous data will be evaluated (action block 170).

If all of the individual match count distributions are normal and contain less than 1% outer data points, the statistical program 106 determines if there are statistical differences between the qualified ABS systems 18' (decision block 176). Specifically, for each non-qualified BQS 12', the statistical program 106 determines if the means of each individual match count distribution (3 for each non-qualified BQS 12') is within the mean ±1.5 times of the remaining two individual match count distributions.

If it is, it will be assumed that there are statistical differences between the qualified ABS systems 18', in which case, the anomalous data will be evaluated (action block 170). If it is not, it will be assumed that there are no statistical differences between the qualified ABS systems 18', in which case, the statistical program 106 will then compute the tolerance intervals for each individual match count distribution (action block 178). In a preferred method, a tolerance interval is defined such that 95% of the MTZ match counts will fall within the tolerance interval at a 99% confidence level. Given these requirements, the tolerance interval can be calculated as the mean±(k×standard deviation), where k=2.3 for 125 runs. If the computed tolerance interval for any of the individual match count distributions includes 0 or 22 MTZ match counts (decision block 180), the anomalous data will be evaluated (action block 170).

If all of the computed tolerance intervals do not include 0 or 22 MTZ match counts (decision block 180), the statistical program 106 pools the statistical MTZ match count data from the three qualified ABS systems 18' for each non-qualified BQS 12' (375 runs), and determines the pooled match count distributions (a total of 4) (action block 182). The statistical program 106 then computes inner and outer working tolerance intervals for each of the pooled match count distributions (action block 184).

In a preferred method, the inner tolerance interval is defined such that 95% of the MTZ match counts will fall within the tolerance interval at a 99% confidence level. Given these requirements, the inner tolerance interval can be calculated as the mean±(k×standard deviation), where k=2.14 for 375 runs. The lower limit of the inner working interval can be determined by rounding the inner tolerance lower limit value up to the next integer value, and the upper limit of the inner working interval can be determined by rounding the inner tolerance upper limit value down to the next integer value.

In a preferred method, the outer tolerance interval is defined such that 99% of the MTZ match counts will fall within the tolerance interval at a 99% confidence level. Given these requirements, the outer tolerance interval can be calculated as the mean±(k×standard deviation), where k=3.0 for 375 runs. The lower limit of the outer working interval can be determined by rounding the outer tolerance lower limit value up to the next integer value, and the upper limit of the outer working interval can be determined by rounding the outer tolerance upper limit value down to the next integer value.

Next, the statistical program 106 determines if the inner or outer tolerance intervals for any of the pooled match count distributions includes 0 or 22 MTZ match counts (decision block 186). If so, the anomalous data will be evaluated (action block 170). If all of the inner and outer tolerance intervals do not include 0 or 22 MTZ match counts (decision block 186), the statistical program 106 then performs a lower range check on each pooled match count distribution (action block 188). The lower range is defined such that 99% of the MTZ match counts will be above the lower range at a 99% confidence level. Given these requirements, the lower range can be calculated as the mean±(k×standard deviation), where k=5.0 for 375 runs. Next, the statistical program 106 determines if the lower range is less than or equal to zero (decision block 190).

If it is, the anomalous data will be evaluated (action block 170). If it is not, the statistical program 106 will determine if the lower limit of the outer tolerance interval for each pooled match count distribution is less than a minimum lower limit (decision block 192). In the illustrated method, the minimum lower limit is 1 if the number of MTZs on the corresponding non-qualified BQS 18' is less than 24, and 2 if the number of MTZ on the corresponding non-qualified BQS 18' is equal to or greater than 24. If the lower limit of the outer tolerance interval is less than the minimum lower limit, the anomalous data will be evaluated (action block 170). If it is not, it is determined if a complete non-qualified BQS set exists (in this case, 4 BQSs make a complete set) (decision block 194). If not, another set of non-qualified BQSs 18' are selected at action block 162, and the process repeats. If so the BQS set will be qualified, and the slide IDs, inner and outer tolerance intervals, and x-y coordinates of the MTZs and fiducial marks will be stored on a suitable medium as the unique BQS data 14 (action block 196).

Figure 10:
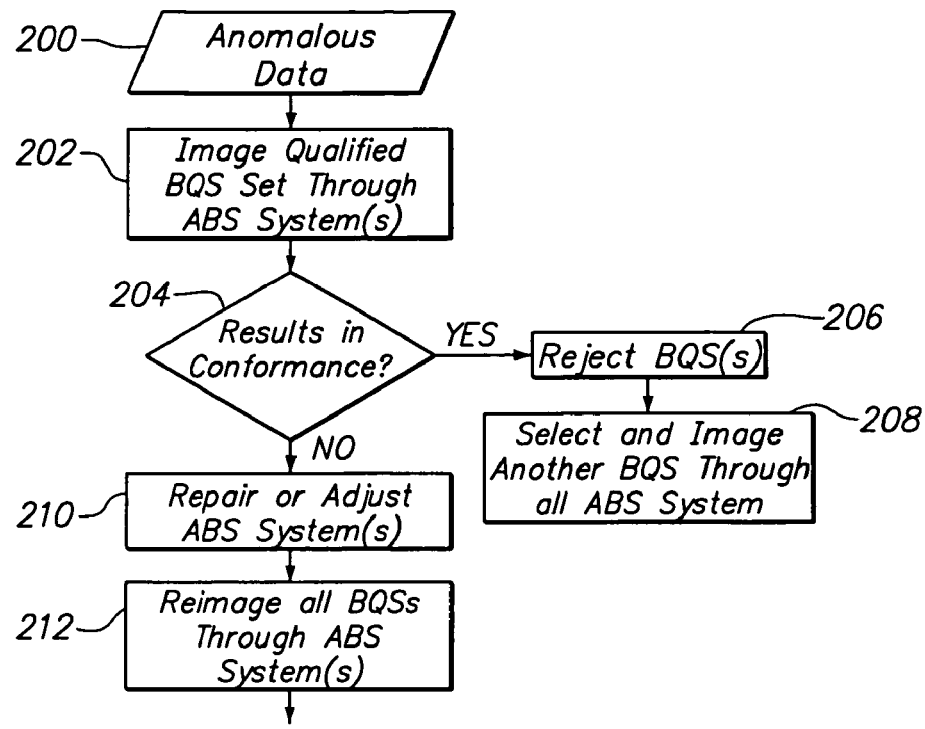
FIG. 10 is a flow diagram illustrating a process used to examine anomalous data that may result from the process of FIG. 9.

Referring now to FIG. 10, any anomalous data generated in the process of FIG. 9 will be analyzed as follows. The process begins with the generation of anomalous data (status block 200). The technician determines the source of the non-conformity by re-running another previously qualified BQS set through the qualified ABS system(s) 18' from which the anomalous data was generated (action block 202). The technician then determines if the results are in conformance (decision block 204). If they are, than the non-conformity can be attributed to the non-qualified BQS 12'. In this case, the non-qualified BQS 12' is rejected (action block 206), and another non-qualified BQS is selected for the non-qualified BQS set, and processed through all of the qualified ABS systems 18' (action block 208). If the results are not in conformance, the non-conformity can be attributed to the qualified ABS system(s) 18' from which the anomalous data was generated, in which case, the qualified ABS system(s) is investigated and repaired or adjusted as necessary (action block 210), and each non-qualified BQS 12' in the set is processed through the qualified ABS system(s) 18' (action block 212).

III. Procedure for Qualifying ABS System

Figure 12:
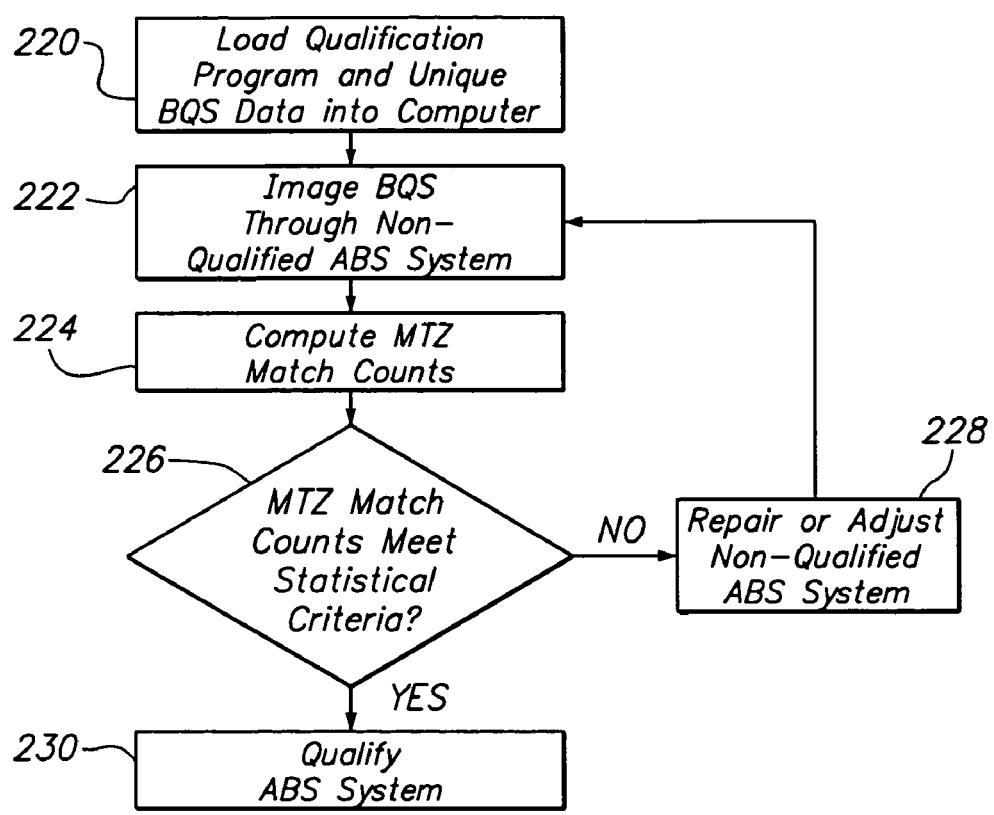
FIG. 12 is a flow diagram illustrating a process used to qualify a non-qualified ABS system with the qualification kit of FIG. 1.

Referring now to FIG. 12, a preferred process of using the qualification kit 10 to qualify the non-qualified ABS system 18 will now be described. First, the qualification program 16 and unique BQS data 14 are loaded into the computer 20 (action block 220). Next, the set of BQSs 12 are processed through the non-qualified ABS system 18, resulting in the generation of FOIs (action block 222). In a preferred method, each BQS 12 is processed through the non-qualified ABS system 18 over two runs. There thus will be a total of 8 runs (assuming that there are four BQSs 12). For each run, the qualification program 16 calculates the number of MTZ matches to obtain a MTZ match count for the respective qualified BQS 12 (action block 224). Specifically, the qualification program 16, for each run, will compare the x-y coordinates of the FOIs generated by the non-qualified ABS system to the x-y coordinates of the MTZs (after transformation into the FOI coordinate system using x-y coordinates of fiducial marks) obtained from the unique BQS data 14. This can be accomplished in the same manner described above with respect to FIG. 11 and the accompanying text.

Next, the qualification program 16 determines if the MTZ match counts (eight in number) meet certain statistical criteria by compared them to the statistical information obtained from the unique BQS data 14 (decision block 226). The statistical criteria can comprise any criteria, but in a preferred method is as follows: (1) the MTZ match counts from each BQS 12 must be within the respective outer tolerance interval defined for that BQS 12 for both runs; (2) the sum of the MTZ match counts from each BQS 12 outside the respective inner tolerance interval defined for that BQS 12 for both runs must not exceed 2; (3) there must be at least one MTZ match for each BQS 12 for each run; (4) for at least six of the runs (out of a total of eight), the MTZ counts for the BQSs 12 must be within the inner tolerance interval defined for the respective BQS 12; and (5) each BQS 12 must have at least one MTZ match count within the inner tolerance interval defined for that BQS 12.

If the MTZ match counts do not meet the defined criteria, the non-qualified ABS system 18 is repaired or adjusted as necessary (action block 228), and the processes returns to action block 222, where the BQSs 12 are again processed through the non-qualified ABS system 18. If the MTZ match counts do meet the defined criteria, the non-qualified ABS system 18 is deemed to be qualified (action block 230).

Although particular embodiments of the present invention have been shown and described, it will be understood that the above discussion is not intended to limit the invention to these embodiments. Those skilled in the art will appreciate that various changes and modifications may be made without departing from the scope of the invention, as defined by the claims.

What is claimed:

1. A method of qualifying an automated biological screening system, comprising:
    providing at least one biological specimen having a plurality of marked target zones (MTZs) exhibiting an attribute;
    processing the at least one biological specimen through the automated biological screening system to determine locations of biological objects suspected of exhibiting the attribute; and
    comparing the locations of the MTZs to the locations of the suspicious biological objects in order to determine a number of matches.

2. The method of claim 1, wherein the at least one biological specimen is carried by a slide.

3. The method of claim 1, wherein the at least one biological specimen comprises a plurality of biological specimens.

4. The method of claim 1, wherein the MTZs comprise cells exhibiting an abnormal attribute.

5. The method of claim 4, wherein the abnormal cells are selected from a group consisting of Low Grade Squamous Intraepithelial Lesions (LGSIL), High Grade Squamous Intraepithelial Lesions (HGSIL), Squamous Cell Carcinoma, Adenocarcinoma, and Adenocarcinoma in situ.

6. The method of claim 1, further comprising qualifying the automated biological screening system based on the number of matches.

7. The method of claim 1, further comprising qualifying the automated biological screening system based on the number of matches and statistical information relating to the MTZs.

8. The method of claim 7, wherein the statistical information comprises a number of match counts between the locations of the MTZs and the locations of suspected biological objects obtained from at least one other automated biological screening system.

9. The method of claim 8, wherein the statistical information comprises a mean, and the automated biological screening system is qualified based on the number of matches relative to the mean.

10. The method of claim 8, wherein the statistical information comprises a tolerance interval, and the automated biological screening system is qualified based on the number of matches that fall within the tolerance interval.

11. The method of claim 10, wherein the tolerance interval is defined such that a predefined percentage of the population is contained within the tolerance interval at at least a predefined confidence level.

12. A method of generating statistical information for a biological specimen, comprising:
 providing at least one biological specimen having a plurality of marked target zones (MTZs) exhibiting an attribute;
 processing the at least one biological specimen through at least one automated biological screening system over a number of runs, wherein locations of biological objects suspected of exhibiting the attribute are determined for each processing run;
 comparing the locations of the MTZs to the locations of the suspicious biological objects in order to determine a number of matches for each run; and
 generating statistical information based on the number of matches for each run.

13. The method of claim 12, wherein the at least one biological specimen is carried by a slide.

14. The method of claim 12, wherein the at least one biological specimen comprises a plurality of biological specimens.

15. The method of claim 12, wherein the at least one automated biological screening system comprises a plurality of automated biological screening systems.

16. The method of claim 12, wherein the MTZs comprise cells exhibiting an abnormality.

17. The method of claim 16, wherein the abnormal cells are selected from a group consisting of Low Grade Squamous Intraepithelial Lesions (LGSIL), High Grade Squamous Intraepithelial Lesions (HGSIL), Squamous Cell Carcinoma, Adenocarcinoma, and Adenocarcinoma in situ.

18. The method of claim 12 wherein the statistical information comprises a number of match counts between the locations of the MTZs and the locations of suspected biological objects obtained from at least one other automated biological screening system.

19. The method of claim 18, wherein the statistical information comprises a mean of the number of matches determined over the runs.

20. The method of claim 18, wherein the statistical information comprises a tolerance interval for the number of matches.

21. The method of claim 20, wherein the tolerance interval is defined such that a predefined percentage of the population is contained within the tolerance interval at at least a predefined confidence level.

* * * * *